United States Patent [19]

Hubelbank et al.

[11] Patent Number: 4,920,489
[45] Date of Patent: Apr. 24, 1990

[54] APPARATUS AND METHOD FOR SOLID STATE STORAGE OF EPISODIC SIGNALS

[75] Inventors: Mark Hubelbank, Sudbury; David Shadmon, Westbury, both of Mass.

[73] Assignee: CardioData Inc., Northboro, Mass.

[21] Appl. No.: 85,879

[22] Filed: Aug. 14, 1987

[51] Int. Cl.⁵ ............................................. G06F 15/42
[52] U.S. Cl. .............................. 364/413.06; 128/702; 128/709; 128/710
[58] Field of Search ............ 364/417, 416, 415, 413.03, 364/413.04, 413.05, 413.06; 128/710, 702, 709

[56] References Cited

U.S. PATENT DOCUMENTS

| | | | |
|---|---|---|---|
| 4,090,505 | 5/1978 | Mortara | 128/710 X |
| 4,193,393 | 3/1980 | Schlager | 128/710 |
| 4,346,718 | 8/1982 | Morris | 128/710 |
| 4,390,972 | 6/1983 | Machida | 371/10 X |
| 4,417,306 | 11/1983 | Citron | 128/710 X |
| 4,475,558 | 10/1984 | Bock | 128/710 |
| 4,519,398 | 5/1985 | Lisiecki | 128/710 |
| 4,653,022 | 3/1987 | Koro | 128/709 X |

FOREIGN PATENT DOCUMENTS

8102832  10/1981  World Int. Prop. O. .......... 128/710

OTHER PUBLICATIONS

Försti et al., "On Line Recording and Analysis of ECG in Ambulatory Patients", Computers in Cardiology, Sept. 1981, pp. 173–175.
Schmitt et al., "ECG Data Compression for the Emergency Setting", Journal of Clinical Engineering, vol. 4, No. 1, Mar. 1979, pp. 49–54.

*Primary Examiner*—Jerry Smith
*Assistant Examiner*—Steven G. Kibby
*Attorney, Agent, or Firm*—Lyon & Lyon

[57] ABSTRACT

A method and apparatus for digitally storing episodic signals, such as, electrocardiogram signals is disclosed. In a preferred embodiment, the apparatus includes, for each signal channel, an input amplifier, an analog-to-digital converter, and a double data buffer. The incoming signal on each channel is converted to a multibit digital number a fixed sampling rate. Each multibit digital number is stored in a location in the double data buffer. When a fixed amount of data is stored in the buffer, a processor examines the data to determine the periods during which the signal is undergoing the most rapid rate of change. For these periods, both an indicator of the period, and a first number of data samples per unit time is stored in a bulk solid state memory. Preferably, the data stored is a number relating to the difference between the value of the sample and a number related to the value of the last sample. For other periods, having rates of data change high, but not as high as those of the first period, a smaller number of samples per unit time is stored. These samples are chosen to faithfully reproduce the minima and maxima of the waveform. For all other waveform periods, every Rth sample is stored. The storage media is preferably dynamic random access memory, the refresh rate of which is determined by the temperature of the circuitry.

91 Claims, 7 Drawing Sheets

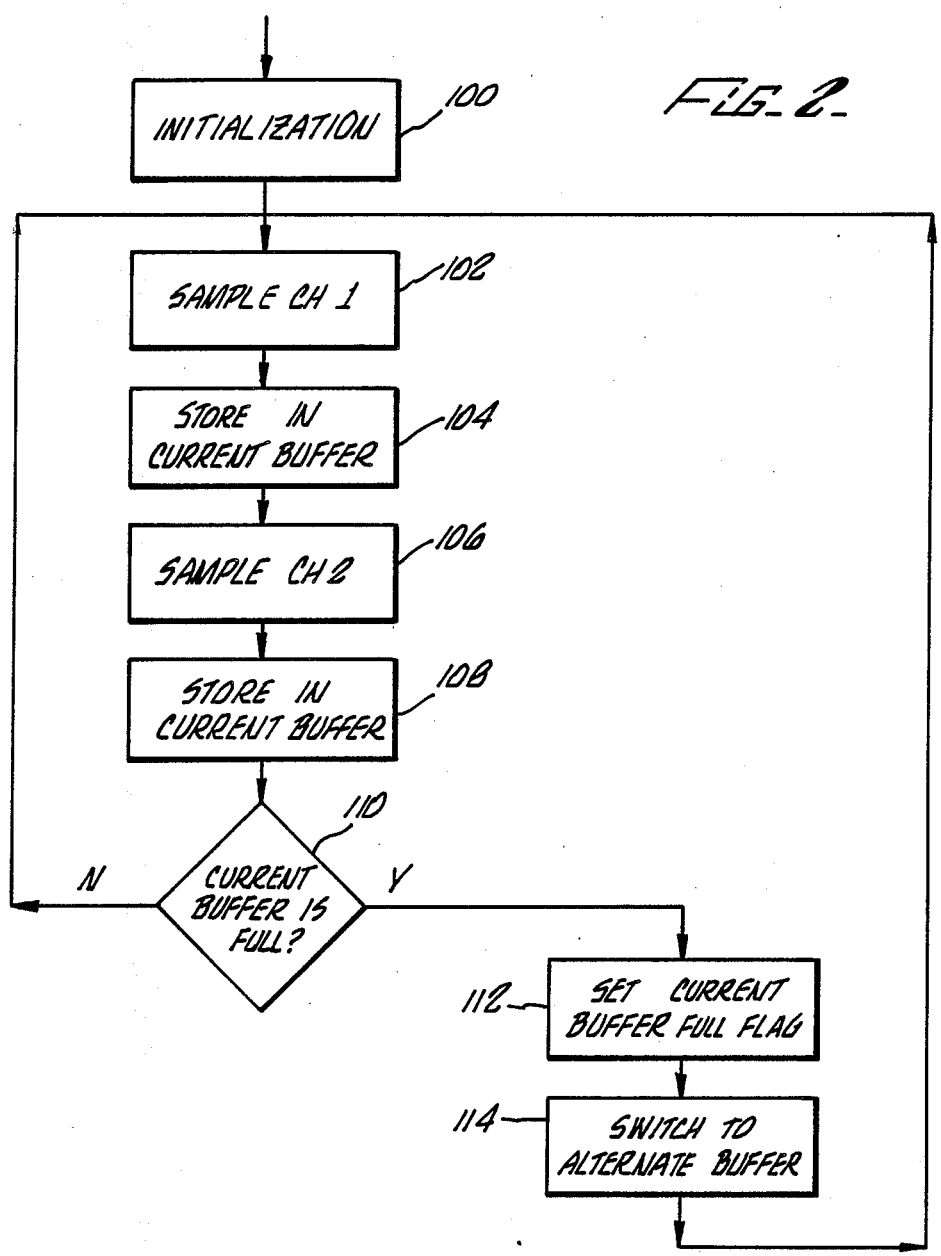
FIG_2.
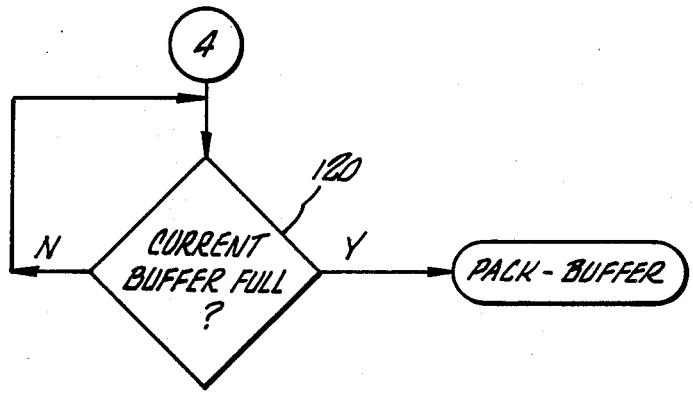
FIG_3.

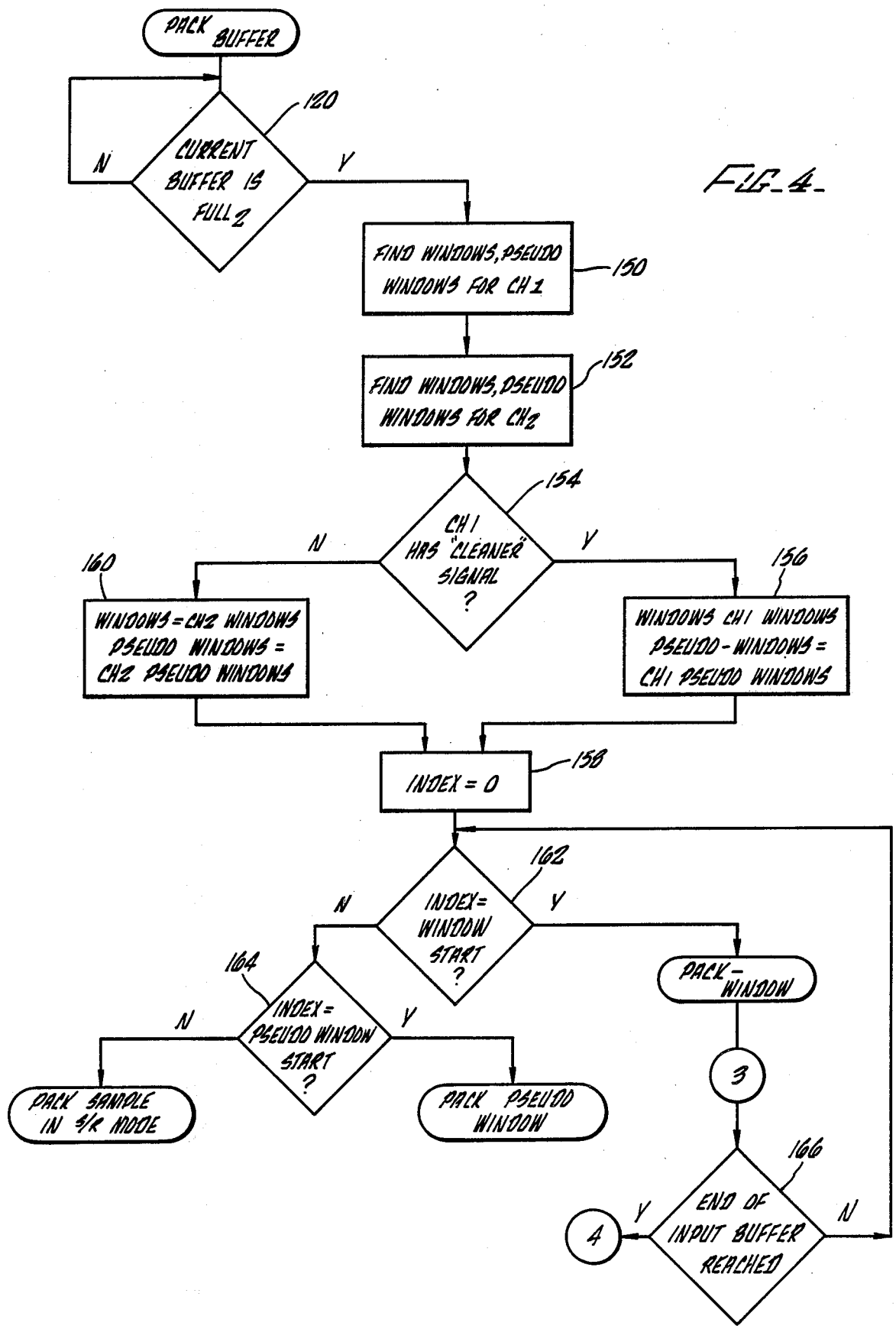

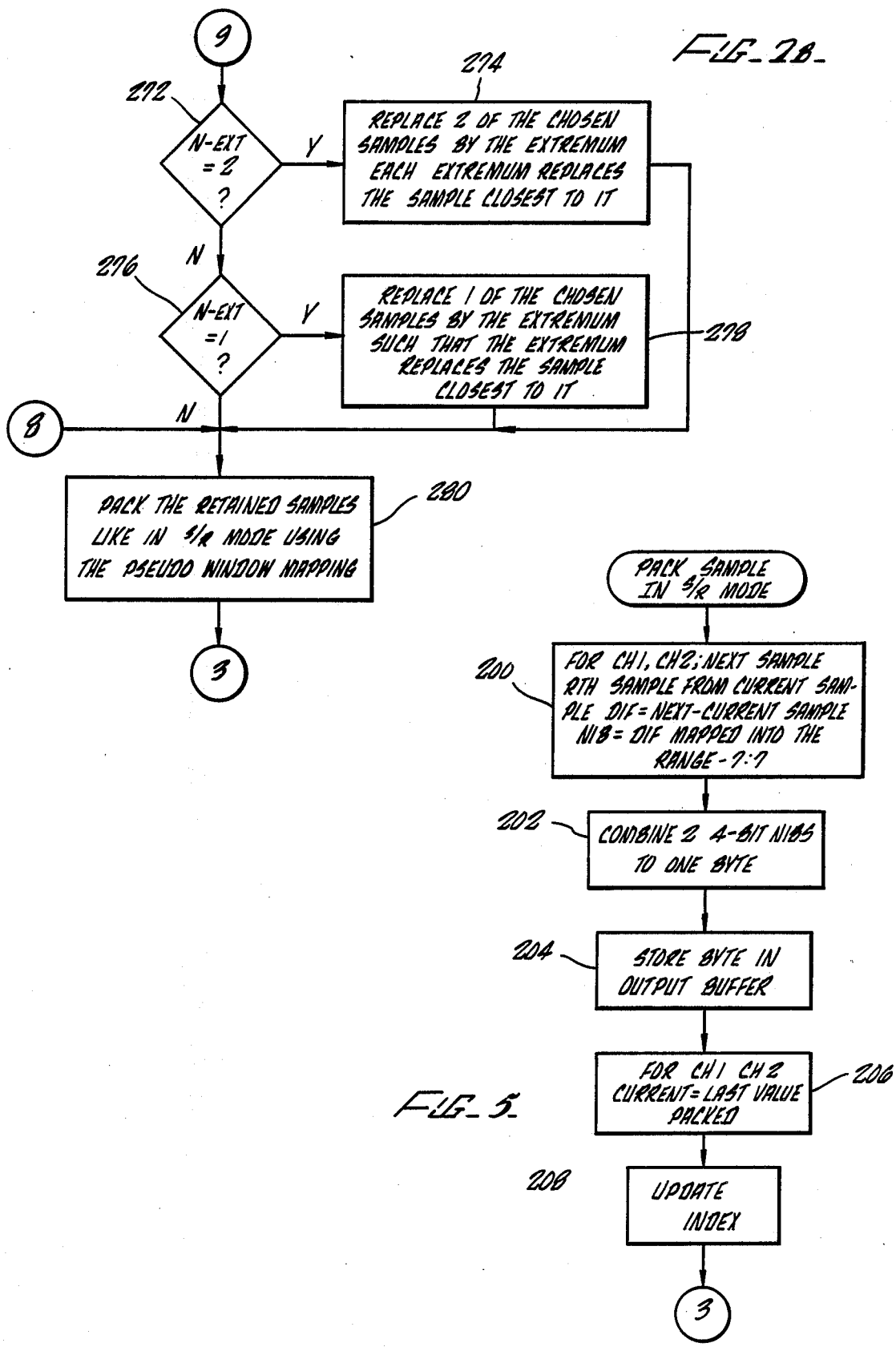

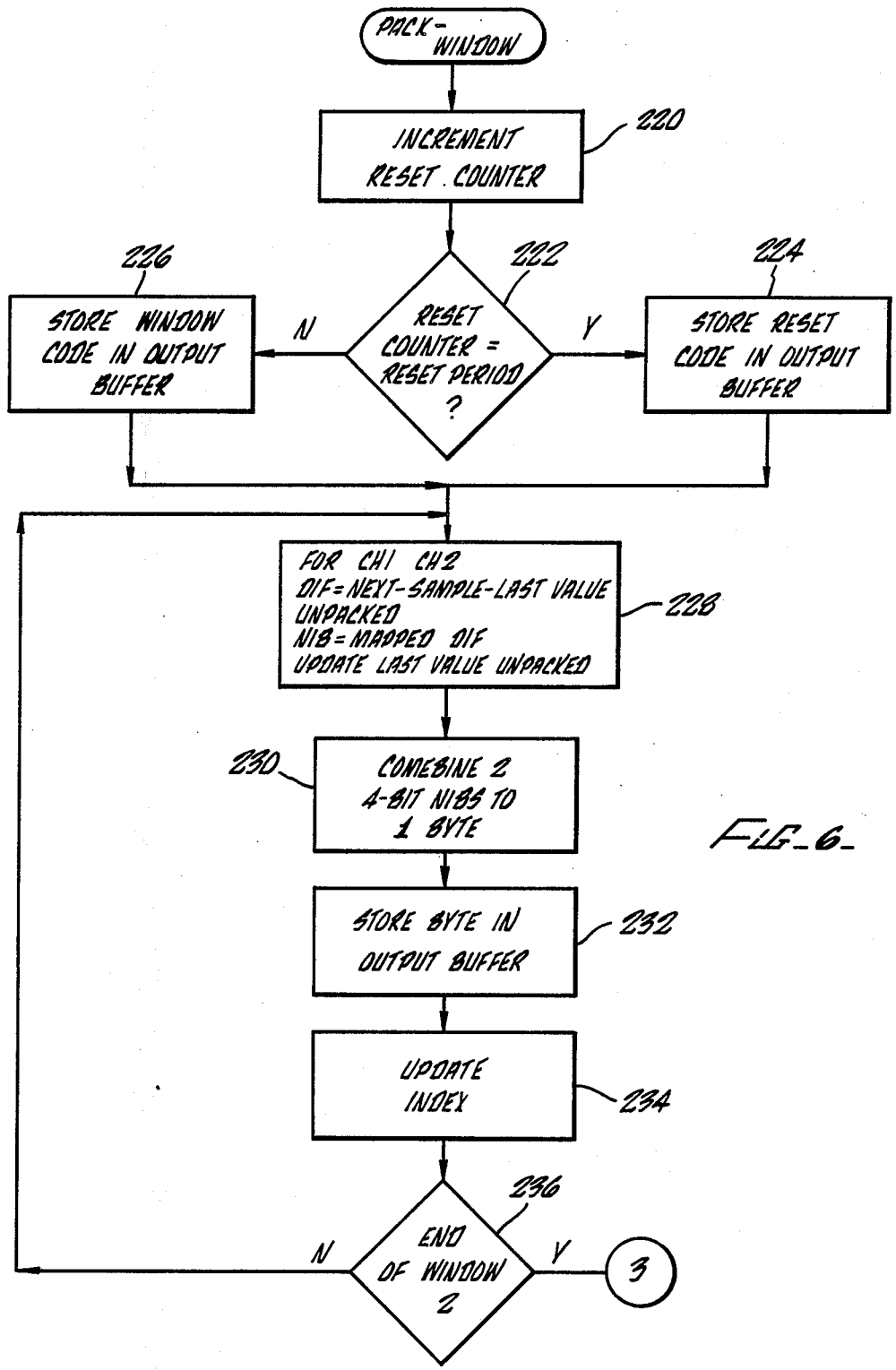
FIG_6_

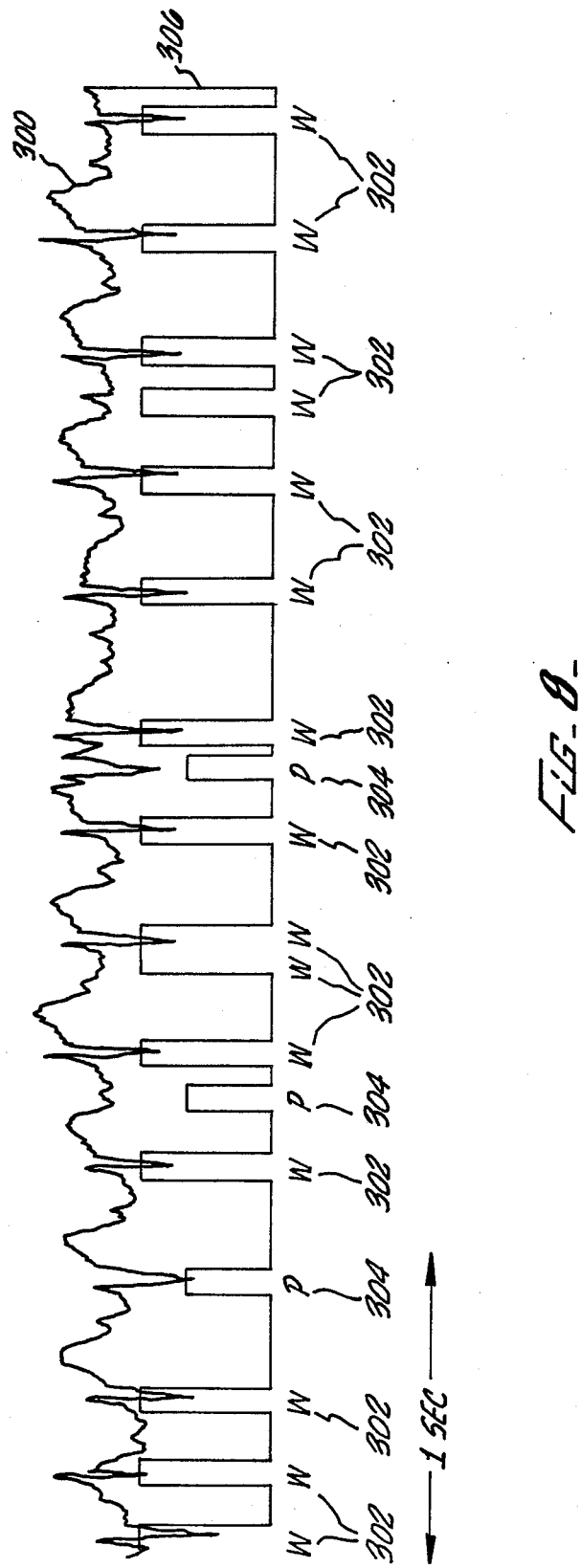

APPARATUS AND METHOD FOR SOLID STATE STORAGE OF EPISODIC SIGNALS

BACKGROUND OF THE INVENTION

1. Field of the Invention

The present invention relates to storage devices for episodic signals, such as electrocardiogram (ECG) signals. More particularly, the present invention relates to storage of ECG signals on portable storage media, which is especially useful for monitoring of ambulatory patients, i.e. a "Holter" type monitors.

2. The Prior Art

Recording of episodic biological signals is known in the art. Such signals, for example ECG signals, have been observed as oscilloscope traces, have been stored in the form of paper chart records, and have been recorded on magnetic tape. It has been customary to record ECG signals on an analog magnetic tape recorder, generally using a direct recording technique. Occasionally, FM, pulse width, or pulse ratio modulation has been used. Today, it is common to record two separate ECG leads for twenty-four hours with a bandwidth that extends from just over 0.05 Hz to an upper limit between 50 and 100 Hz.

Direct digital storage is desirable to achieve lower weight and higher reliability than is possible with mechanical tape recording components. Semiconductor memory is available that would, in theory, permit such storage. Unfortunately, the present state of the art of semiconductor memory is such that memory chips are relatively expensive, take up a fair amount of circuit board space, and consume a fair amount of power. It is thus highly desirable to limit, where possible, the number of memory components in a system.

This present limitation of semiconductor memory presents a potential memory size problem. It has been experimentally determined that in order to digitally store an ECG signal with the fidelity necessary for accurate processing and visual reconstruction, it is necessary to sample the ECG at a rate of at least 125 samples per second. By performing some "automatic gain control," data may be stored in a processing computer as one byte per data point. If the data were stored directly at a rate of 125 samples per second, it would require 21.6 megabytes of storage to store two channels of ECG for twenty-four hours.

While there are semiconductor memory chips available today with densities as great as one megabit per chip, it is apparent that direct recording of the ECG signal for twenty-four hours at the rate of 125 samples per second would require the use of one hundred seventy two separate one megabit memory chips. From the standpoints of cost, power consumption and physical size, this requirement renders direct digital storage somewhat impractical for portable devices, unless some sort of data compression is employed.

In the literature, there is significant reference to a variety of algorithms for compression of the ECG data to minimize the amount of data to be stored. The most prominent among these are, Cox, J. R., Nolle, F. M., Fozzard, H. A. and Oliver, G. C., Jr. "AZTEC-A Preprocessing Program For Real Time ECG Analysis," IEEE Trans on Bio-Med Eng. (Short Commun.), Vol. BME-15, pp 128-129, April 1968; Mueller, William C., "Arrythmia Detection Program For An Ambulatory ECG Monitor," BIOMEDICAL SCIENCES INSTRUMENTATION Vol 14, PAGE 81, 1978; Hambly, Alan R., Moruzzi, Romeo L. and Feldmen, Charles L. "The Use Of Intrinsic Components In An ECG Filter," IEEE Trans On Bio-Med Eng. Vol. BME-21, No. 6 pp 469-476, November 1974.

While each of these data compression processes has some utility, each has inadequacies which make it unsuitable for the present application. There is thus a need for an apparatus which is capable of performing direct digital storage of the ECG signals and a method of storing these signals which provides suitable data compression for lowering the amount of memory required, while at the same time obtaining the capability to faithfully reproduce the important characteristics of an ECG signal.

BRIEF DESCRIPTION OF THE INVENTION

The present invention includes apparatus and a method for direct digital storage of episodic signals, such as ECG signals, including data compression.

Apparatus of the present invention includes a front-end analog processor, typically a simple amplifier/band limiting circuit, which conditions the ECG signal from each lead. An analog to digital converter converts the conditioned analog signal to a proportional digital word at a sampling rate determined by the compression scheme employed. The data is buffered, then compressed by a digital processor. A digital memory comprising semiconductor memory chips, preferably DRAMs, is then used to store the digitized data. The memory manipulations and data compression algorithm are controlled by suitable intelligence, which may be a microprocessor. The microprocessor also controls the refresh rate of the DRAMs, which is varied with the temperature of the circuitry.

The invention may also include optional facilities for storage of other events, such as a tag indicating the presence of an artificial pacemaker spike, the switching of an event marker, the value of a patient's blood pressure, etc. These optional events are detected by other means and may be inserted into the memory in any convenient manner.

An important element of the present invention is the data compression processor. It is designed to minimize the amount of storage required to store data from signals characterized by short periods of rapidly changing values separated by relatively long periods of slowly changing values, referred to herein as episodic signals. An example of this kind of data is the rapidly-changing QRS complex of the ECG, which typically occurs at a rate of 50 to 200 times per minute separated by relatively slowly varying P,T, and U waves and several isoelectric portions. There are other waveforms that occur in living species that have similar characteristics, such as the spike and wave of the EEG, various types of evoked responses, the episodic discharge patterns of peripheral nerves, and various analogs of muscular contractions. Similar types of signals also occur in the non-biological world. The present invention is useful for digital storage of such signals. While the disclosure herein will be with respect to ECG signals, those of ordinary skill in the art will appreciate that this is by way of illustration and that other episodic signals way be stored using the disclosed method and apparatus.

In a presently-preferred embodiment of the present invention, the amplitude of the ECG signal is sampled and the derivative of the signal is measured at each sample. Samples are taken at the rate of S per unit time, and the sampling ratio R, the ratio of the number of samples taken to the number actually stored, is selected to minimize both the number of samples retained and the amount of data which would be lost by undersampling. In a presently-preferred embodiment, S is chosen to be 180 samples per second and R is chosen to have one of two values, either 1 or 3. The value R=1 is used when the signal has the highest rate of change. The periods of R=1 are referred to herein as "windows". Further, because the occurrence of more than 3 QRS complexes per second is extremely unusual, the process allows only three windows or periods of R equal to 1 to occur each second and in a preferred embodiment these are each fifteen samples wide, generally more than the width of a QRS complex.

Although it is unusual to have more than three QRS complexes per second, it is not unusual to have artifact superimposed on the ECG signal. This need not be reproduced with high fidelity, but it should look like the original artifact. Accordingly, in a preferred embodiment there are intervals designated as pseudo-windows which are used when the sum of the absolute differences between adjacent samples exceeds a predetermined threshold. The pseudo-windows are preferably fifteen samples wide and consist of samples chosen from among the fifteen samples to maintain the number and magnitude of the peaks of the pseudo-windows but to allow the exact wave shape to vary from the original.

For all other samples, R is chosen as 3. To assure that the periods of R equal to 1 are chosen appropriately, all samples are stored in a temporary buffer for at least one second and the windows and the pseudo-windows are selected from among all of the samples taken during the second according to the periods in which the sums of the absolute value of the derivative of the signal is highest.

The data stored is a number related to the amplitude value of the sample. It may be the digitized value of the sample itself, a digital number related to the value of the sample, or the differences between adjacent stored samples. Data compression, preferably by means of storage of first derivatives, may also be employed in the present invention. Rather than storing the absolute values of the sampled data, the differences in amplitude between adjacent samples may be stored. These differences are preferably mapped into a preselected range of values in a non-linear manner. Further, the mapping may be different, depending on whether the data is contained in a window, a pseudo-window, or neither.

BRIEF DESCRIPTION OF THE DRAWINGS

FIG. 3 illustrates the main program loop utilized in a preferred embodiment of the present invention.

FIG. 4 is a flow diagram showing the packing of a buffer according to a preferred embodiment of the present invention.

FIG. 5 is a flow diagram showing the packing of one sample in S/R mode utilizing a preferred embodiment of the present invention.

FIG. 6 shows a flow diagram illustrating the packing of one window according to a preferred embodiment of the present invention.

FIGS. 7a and 7b are flow diagrams showing the packing of a pseudo-window according to a preferred embodiment of the present invention.

FIG. 7 demonstrates the relationship between FIGS. 7a and 7b.

FIG. 8 is an illustrative ECG trace showing how a typical ECG signal segment is divided into windows and pseudo-windows.

DETAILED DESCRIPTION OF A PREFERRED EMBODIMENT

Figure 1:
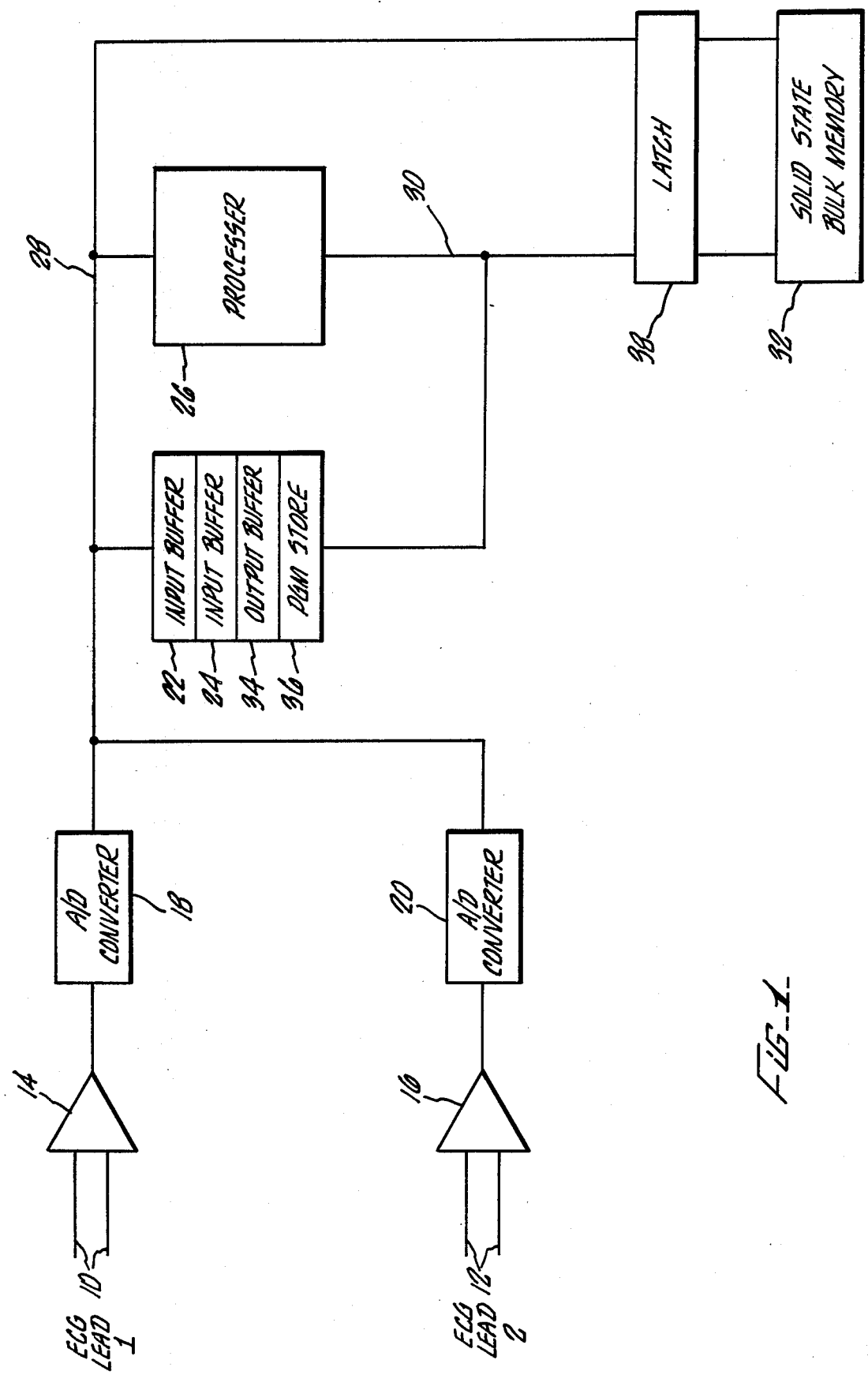
FIG. 1 is a block diagram of the components of a preferred embodiment of the present invention.

Referring first to FIG. 1, a block diagram of apparatus configured according to a preferred embodiment of the present invention, a first set of ECG leads 10 and a second set of ECG leads 12 are connected to amplifiers 14 and 16 respectively. This will be readily understood by those of ordinary skill in the art. Amplifiers 14 and 16 may be low power operational amplifiers, such as the TL064 manufactured by Texas Instruments. Suitable means, such as an integrator feedback arrangement, apparent to those of ordinary skill in the art, should be employed to minimize DC offset at the outputs of amplifiers 14 and 16. Those of ordinary skill in the art will understand that suitable high-pass filtering should also be employed. A high-pass filter with a cutoff frequency of at least 0.05 Hz is recommended.

The outputs of amplifiers 14 and 16 are fed to A/D converters 18 and 20 respectively. A/D converters 18 and 20 are identical, and, in a preferred embodiment herein, are 8 bit A/D converters having a signed output in the range $-128$ to $+127$.

The outputs of A/D converters 18 and 20 are tristated onto a data bus and are fed to data input buffers 22 and 24, respectively, in a conventional manner. Data input buffers 22 and 24 may be configured from random access memory.

As can be readily seen by those of ordinary skill in the art, the ECG lead 10, amplifier 14, A/D converter 18 and data input buffer 22 form a first input channel of the apparatus of the present invention. Similarly, ECG lead 12, amplifier 16, A/D converter, and data input buffer 24 form a second input channel of the apparatus of the present invention.

Data input buffers 22 and 24 are accessible by processor 26 via the data bus 28 and an address bus 30. Processor 26 also has access to solid state bulk memory 32 via the data and address busses 28 and 30. Processor 26 can access output buffer 34 via the busses. Output buffer 34 may also be configured from random access memory. A 32k byte random access memory can be used to form data input buffers 22 and 24, output buffer 34, as well as program store 36 for processor 26. Low power memory should be used to minimize battery consumption.

Processor 26 may be any one of many available 8 bit microprocessors, such as the 68HC11 manufactured by Motorola. It has been found satisfactory to operate this processor at a clock frequency of 2 MHz.

Solid state bulk memory 32 may be configured by random access memory, or other similar memory. Currently, it is preferable to configure solid state bulk memory storage 30 from 64 one-megabit dynamic random access memory devices (DRAMs), having low standby current. The Toshiba TC511000P/J-12 has been found to be satisfactory.

In normal operation, DRAM devices must be periodically refreshed. The recommended refresh rate for such devices is in the neighborhood of eight milliseconds. This refresh rate is based typically upon worst-case operating conditions including temperature. Most DRAM devices are rated to 70° C. When DRAMs are used in apparatus according to the present invention, it is not likely that the operating temperature of such devices will exceed 45° C. This being the case, significant de-rating of the refresh rate is possible. At room temperature, i.e., 25° C., a refresh cycle every 150 milliseconds has been found to be satisfactory for the present invention, while at 45° C. a refresh cycle every 80 milliseconds has been found to be satisfactory for the present invention. In the presently-preferred embodiment the refresh rate should change approximately exponentially with temperature, although those of ordinary skill in the art will realize that a linear change or other change will function. By significantly decreasing battery power consumption, the present invention makes possible truly "portable" solid state ECG storage units. A thermosensor may be incorporated in apparatus of the present invention to determine the operating temperature of the components. This sensor may be used in a conventional manner to control circuitry which directs the initiation of refresh cycles for the DRAMs from a rate of approximately 150 mSec. at room temperature to one of 80 mSec at 45° C. By so controlling the refresh rate of the DRAMs, power consumption is significantly lowered without sacrificing data retention.

In a preferred embodiment, thermistor 40 and resistor 42 form a voltage divider, the output of which is digitized by an A/D converter inside of processor 26. Processor 26 in turn controls the refreshing of the DRAMs at a rate controlled by a table accessed by processor 26 using the value digitized from the voltage divider. Use of processors to control refresh of DRAMs is known. One novel feature of the present invention is to adjust the refresh rate according to the ambient temperature.

A major function of processor 26 is to compress the raw data stored in data input buffers 22 or 24 and store the compressed data in such a way that 24 hours of ECG signals may be reproduced to enable later ECG analysis. Operation of processor 26 and solid state bulk memory 32 will be described with reference to FIGS. 2 through 7.

Power consumption aside, the problem of storing 24 hours of ECG signals in portable apparatus utilizing solid state memory is largely a problem of data compression. In order to directly store the ECG signals digitally without data compression with the fidelity necessary for accurate processing and visual reconstruction, it is necessary to sample the ECG at a rate of at least 125 samples per second. Processing and storage schemes using direct digital storage at a rate of 125 samples per second would require 21.6 megabytes of storage to store two channels of ECG for 24 hours. The straightforward solution is, thus, somewhat impractical for portable applications.

The method and apparatus of the present invention therefore includes a data compression and data packing scheme which allows the storage of two channels of ECG signals over a 24 hour period, utilizing only 8 megabytes of storage space.

The scheme utilized in the present invention consists of three conceptual stages: sampling data; choosing data samples for packing; and packing data.

In a presently-preferred embodiment, each data sample is an 8-bit signed number, in the range $-128$ to $127$. Those of ordinary skill in the art will readily realize that other formats may be used. In this embodiment, the 24 hours of two-channel 8-bit ECG data is stored into 8 megabytes of memory by virtue of data compression techniques, using 4 bits for each packed value. With these parameters, the number of bytes which can be packed per second is $2^{23} \times 8/(24 \times 3600 \times 2 \times 4) = 97.09$, where $2^{23}$ = the number of available bytes; 8 = the number of bits per byte; 24 = the number of hours; 3600 = the number of seconds per hour; 2 = the number of channels; and 4 = the number of bits per packed value. In this embodiment, only 90 bytes per second are actually used, and the excess, 7.09 bytes, may be used for special codes which will be described hereinafter.

A straightforward scheme with a sampling rate of 90 samples per second will not reproduce QRS complexes with fidelity. The scheme utilized in a preferred embodiment of present invention has an effective data rate of 90 bytes per second, i.e., 90 bytes are stored for each second, but they originate from two different actual sampling rates. In a presently-preferred embodiment, the two actual sampling rates used are 60 samples per second and 180 samples per second. When the ECG is stable, 60 samples per second are adequate. When there are large differences between adjacent samples, a higher sampling rate, such as 180 samples per second, is needed. Those of ordinary skill in the art will understand that two actual sampling rates of around 33 and 100 samples per second or greater will be satisfactory for the present invention.

According to a presently-preferred embodiment, "windows" are defined for periods in which the differences between adjacent samples are the highest. In a presently-preferred embodiment, three windows of 15 samples each are designated for each second. Thus, from every group of 180 samples, 45 samples at 180 samples per second are retained. From the other 135 samples remaining, one out of every three is taken, representing the 45 additional retained samples to make a total of 90 samples. In all, 45 samples in windows are taken and 45 samples not in windows are taken. While three windows of fifteen samples each is presently preferred, those of ordinary skill in the art will appreciate that other functioning embodiments are possible, and will depend upon the sampling rate, the heart rate, the amount of artifact, etc.

After buffers 22 and 24 have been filled with 8-bit signed samples, processor 26 analyzes the data samples to identify the windows. According to the present invention, either a fixed or a variable number of windows may be designated for each second. The choice between a fixed number of windows and a variable number of windows per second represents a trade-off between simplicity and accuracy in reproducing wave forms with heart rates greater than 180 or those with artifacts. If a fixed number, for instance 3, windows are allowed per second, but the heart rate is, for instance, 60, only one window might actually be needed. If, however, there is significant artifact present, one window might be insufficient. Thus the selection of data for packing according to the present invention may proceed according to one of at least two embodiments.

In the first preferred embodiment, a fixed predetermined number of windows, e.g., three, is allowed for each second. In a second embodiment, a window is designated only if the sum of the differences between the adjacent samples in a window exceeds a predetermined threshold. For example, if there is only 1 QRS complex within a certain second, only 1 window will be used, unless, of course, there is artifact present. Assuming no artifacts, the total number of 4-bit nibbles packed for this second will be 70, i.e., 15 (for the window) plus (180-15)/3. This allows a savings of up to 20 4-bit nibbles which were not used and can thus be used later.

If the first embodiment is used, with 3 windows per second, something must be done to account for heart rates greater than 180 and for artifacts. This is accomplished using the concept of "pseudo-windows". Pseudo-windows are sequences of samples of portions of the ECG signal in which there is a high rate of change between adjacent samples. The packing scheme for pseudo-windows will be described later. It is to be noted that, in the implementation of the preferred embodiment, the pseudo-window sampling ratio is equal to R, the sampling ratio of the S/R mode. The difference between a pseudo-window and an S/R mode sample is that, in a pseudo-window, values of samples for storage are chosen by use of an algorithm which takes into account the need to reproduce the general shape of the artifact. In the S/R mode, only one out of R samples in order are retained.

In an alternate embodiment, using a variable number of windows, the window is designated only if the sums of the differences between adjacent samples in a window interval of samples exceeds a certain predetermined threshold. Currently, using the tables and other conditions stated herein for the preferred embodiment, that threshold is 40.

Data input buffers 22 and 24 preferably have a data capacity large enough to accommodate one second's worth of samples. For instance, if 180 samples/second are taken, the buffers 22 and 24 should have a capacity of at least 180 bytes of data. Preferably, data buffers 22 and 24 should have additional capacity of at least one window interval of bytes beyond one second. In this way, data will be able to be successfully compressed even if, in worst case, a window begins in the last data byte of a one second timing interval, because the compression determination will be able to take into account a window beginning on the last byte of a current second and extending into a next second. Preferably, buffers 22 and 24 are double buffers, so that one buffer may be filled while the processor 26 is acting on the data contained in the other as is known in the art.

When buffers 22 and 24 are full, the data in the buffers is examined to discern how it is to be packed. In a preferred embodiment, the data is examined in 1-window intervals (WI). The following discussion will be made assuming that a window size is 15 consecutive samples wide (i.e., WI=15), but those of ordinary skill in the art will readily understand that a number of samples other than 15 may be used to constitute a window interval. In order to define the windows, the first WI samples within the data buffer are examined. In this illustrative case, samples 1 through 15 are examined. Each sample is compared with the next consecutive sample and the absolute difference (magnitude only, the sign of the difference is ignored) between adjacent samples is computed and stored. The sum of these absolute differences between the WI group samples is computed.

The same procedure is then performed with respect to samples number 2 through 16, and then 3 through 17 etc., until all groups of consecutive WI number of samples have had the sums of the absolute differences between them computed.

After the sums of the absolute differences have been computed, a predetermined number of groups of WI data samples having the largest sums are identified. In a first preferred embodiment, the three highest absolute difference sums are identified. The consecutive groups of WI samples for which these sums are the largest are designated as windows and their starting bytes identified.

In a presently-preferred embodiment, window intervals are not permitted to overlap. One way of preventing window overlap is to identify WI groups of samples with high sums which overlap and to ignore the WI group having the lowest sum of differences. Other ways will readily suggest themselves to those of ordinary skill in the art.

In a presently-preferred embodiment, window starts are adjusted to begin at interval divisible by R, where R is the sampling ratio. This adjustment may, in some cases, take care of otherwise overlapping windows, as well as make simpler later interpoliative reconstruction of S/R mode samples.

To determine the existence of pseudo-windows, the remaining highest sums from a group of WI adjacent samples which have not been chosen as windows are compared with a preset threshold value. A predetermined number of these groups of WI samples will be designated as a pseudo-window only if the sum of the absolute differences between adjacent samples exceeds this given threshold. In a presently-preferred embodiment this threshold is set equal to 40 and only one pseudo window is allowed per second. Thus, any group of 15 consecutive samples is designated as a pseudo-window only if the sum of the absolute differences between adjacent samples within the group of WI samples is greater than 40. If there is more than one such group, the one with the highest sum is selected. The starting byte of each pseudo-window is identified.

Next, the effect of artifacts on the quality of the unpacked waveform is minimized by identifying which of the channels has the "cleanest" signal. In a presently-preferred embodiment, the channel having the cleanest signal is then used to pack the data, i.e., the data for both channels is packed using the "clean" channel's windows and pseudo-windows. In a preferred embodiment, for each channel the number of windows is counted whose absolute sum of differences is greater than a certain predetermined threshold. In a presently preferred embodiment this threshold, like the threshold to determine the existence of a pseudo-window, is 40. Those of ordinary skill in the art will appreciate that, at the expense of some memory space, this step need not be performed, and that both channels may be independently partitioned into windows and pseudo-windows.

If the channel which had been chosen in the most recently passed second has no windows above the threshold, or if it has more than 3 windows above the threshold and the other channel has between 1 and 3 windows above the threshold, the channels are switched and the other channel is used. Thus, if possible, the channel is chosen which has between 1 and 3 windows above the threshold. If a channel has no windows, it is assumed to be an error or a long isoelectric portion of the signal, since there should be at least one QRS complex per second. It should be apparent, however, that if neither channel has a window, it is not necessarily an error, but is a possible condition and it doesn't matter which channel is selected. At this point in time each input sample can now belong to one of three catagories as defined by the chosen channel: it is within a window; it is within a pseudo-window; or it is within neither.

As previously mentioned, data from each channel is stored in memory as 4-bit nibbles which are related to the difference between adjacent samples. In a presently-preferred embodiment, these 4-bit nibbles will have a signed value of from −7 to 7, into which range the differences between the current sample and the last unpacked sample is mapped.

There are three different packing modes used. Samples which are outside of windows or pseudo-windows are packed in S/R mode. In S/R mode, each Rth sample is selected. Those of ordinary skill in the art will appreciate that R and S are related in that if S increases, R may be increased approximately proportionally to achieve the same result. In this sense, R is a function of S. R should be chosen to allow faithful reproduction of the portions of the signal which are relatively steady, such that storage space is not wasted by over-storage but the signal is not distorted by under-storage. Where R=3, every third sample is packed. At the preferred sampling rate of 180/sec, values of R between 2 and 6 should function satisfactorily.

Table 1 shows how the range of differences is mapped into the range −7 to 7 for S/R mode, using a non-linear scale. Table 1 also shows how the range of −7 to 7 is unpacked.

TABLE I

| range of differences | mapped into | unpacked-to |
|---|---|---|
| −255:−27 | −7 | −35 |
| −26:−15 | −6 | −19 |
| −14:−8 | −5 | −10 |
| −7:−5 | −4 | −6 |
| −4:−3 | −3 | −3 |
| −2 | −2 | −2 |
| −1 | −1 | −1 |
| 0 | 0 | 0 |
| 1 | 1 | 1 |
| 2 | 2 | 2 |
| 3:4 | 3 | 3 |
| 5:7 | 4 | 6 |
| 8:14 | 5 | 10 |
| 15:26 | 6 | 19 |
| 27:255 | 7 | 35 |

Table Ia gives an example of successive nibbles of data packed according to Table Ia, and shows how packing and unpacking is accomplished.

TABLE Ia

| Original magnitude | difference from last unpacked value | 4-bit value packed | last value unpacked |
|---|---|---|---|
| 0 | — | — | 0 (initial) |
| 5 | 5 | 4 | 6 |
| 8 | 2 | 2 | 8 |
| 2 | −6 | −4 | −2 |

From Table Ia, it can be seen that the second value unpacked was 6, while the original was 5, but the third value is already equal to the original.

Samples which are inside a window are packed as follows. First, an 8-bit code byte is stored, which denotes the starting of a window in the packed data stream. Code bytes may be used to denote other special cases in the packed data, and they are of the form 8X (hexadecimal), where 8 is the 4-bit binary number 1000, uniquely identifying a code byte, and X is a 4-bit value denoting one of a few special cases like a window-start, a pseudo-window start, etc. The assignment of meanings to the 4-bit binary code byte values is, of course, wholly arbitrary. It is sufficient to note that there are sixteen choices, giving the user the latitude to denote such things as blood pressure, temperature, etc. Particular choices are limited only by the imagination of the user. The particular code byte will inherently designate the numbers of following 8-bit bytes with which it is to be associated. Following the code are WI bytes of data, representing each sample within the window. Each consists of 2 4-bit values, one for each channel.

As in the S/R mode, the difference between the current sample and the last value unpacked is calculated and mapped into the range −7:7, using a non-linear scale. In a preferred embodiment, this non-linear scale is different from the one used for the S/R mode, and is shown in Table II.

TABLE II

| range of differences | mapped into | unpacked-to |
|---|---|---|
| −255:−55 | −7 | −70 |
| −54:−30 | −6 | −38 |
| −29:−17 | −5 | −21 |
| −16:−9 | −4 | −12 |
| −8:−5 | −3 | −6 |
| −4:−3 | −2 | −4 |
| −2:−1 | −1 | −2 |
| 0 | 0 | 0 |
| 1:2 | 1 | 2 |
| 3:4 | 2 | 4 |
| 5:8 | 3 | 6 |
| 9:16 | 4 | 12 |
| 17:29 | 5 | 21 |
| 30:54 | 6 | 38 |
| 55:255 | 7 | 70 |

In order to facilitate error correction, every predefined number of seconds, (the Reset Period), a special Reset Period code byte may be stored for the first window of that second. This code byte indicates a window with original values. The code byte is followed by two bytes, representing the original samples, one for each channel. Thus, an error in the packing or unpacking process, or a transient hardware failure, will effect no more than a reset period number of seconds. Following the original values are WI-1 number of bytes representing the remainder of the samples within the windows as mapped into differences as above. Either Reset Period Code byte, followed by the two 8-bit sample values, or zero is always stored as the first entry in memory to aid in unpacking and signal reconstruction.

As previously mentioned, a pseudo-window of the current channel will be used if its sum of absolute differences is greater than a certain threshold. If that threshold is exceeded and a pseudo-window is to be stored, a code byte is first stored denoting a pseudo-window. In a preferred embodiment, its samples are then packed as in the S/R packing mode, the number of samples to be packed for one pseudo-window is the pseudo-window sample size divided by R. In the presently preferred embodiment it is 15/3=5.

Unlike the S/R mode however, the goal is now to choose the 5 out of the 15 samples which will best reproduce the original waveform. To achieve this result, the selection is made as follows.

The last sample point of the pseudo-window is always chosen, in order to preserve continuity with the following samples. Thus, it remains to choose 4 out of the remaining 14 samples. As a default condition, 4 equally-spaced samples, namely the first, fourth, seventh, and tenth samples are chosen. Next, the number of the extremum (minimum or maximum) points within the pseudo-window is determined. This number is designated herein as N-Ext. If N-Ext is equal to or greater than 4, the 4 extremum points with the highest absolute value are chosen. If N-Ext equals 3, the 3 extremum points and one sample from the longest interval between retained points is chosen. If N-Ext equals 2, the two of the previously chosen samples are replaced by the two extrema such that an extremum replaces the sample closest to it. For example, if the third and eighth samples are extreme points they will replace the fourth and seventh samples, respectively, and the samples retained will be first, third, eighth, tenth, and fifteenth.

If N-Ext equals 1, the extreme number replaces the sample closest to it. If N-Ext equals 0, the default condition obtains and the first, fourth, seventh and tenth samples are retained.

Once the 5 samples have been chosen, they are treated as S/R mode samples. They are mapped into the range −7:7 using a non-linear scale. In the presently-preferred embodiment Table III shows how this range of differences is mapped and unpacked.

TABLE III

| range of differences | mapped into | unpacked-to |
|---|---|---|
| −255:−83 | −7 | −105 |
| −82:−45 | −6 | −57 |
| −44:−25 | −5 | −30 |
| −24:−15 | −4 | −18 |
| −14:−8 | −3 | −9 |
| −7:−5 | −2 | −6 |
| −4:−2 | −1 | −3 |
| −1:1 | 0 | 0 |
| 2:4 | 1 | 3 |
| 5:7 | 2 | 6 |
| 8:14 | 3 | 9 |
| 15:24 | 4 | 18 |
| 25:44 | 5 | 30 |
| 45:82 | 6 | 57 |
| 83:255 | 7 | 105 |

Tables I, II, and III were empirically derived and optimized for ECG signals. As will be observed by those of ordinary skill in the art, the primary differences between Tables I, II, and III are in the range of differences and in the unpacked-to values. The unpacked-to values increase from Tables I to II to III, to take advantage of the fact that the S/R mode samples are taken in periods where the signal is not changing very rapidly, and to take into account that the window and pseudo-window interval samples are taken for periods where the waveform is changing more rapidly and undergoing larger amplitude excursions, as well as the fact that in the pseudo-windows, not every sample is stored, thus leading to a need to unpack the range of differences to a larger number. Those of ordinary skill in the art will realize that, while Tables I, II, and III are believed by the present inventors to have been optimized, other values are possible for these tables without departing from the spirit of the present invention. Such persons will also be easily able to formulate similar tables for use with ECG signals as well as with other episodic signals.

Figure 2A:
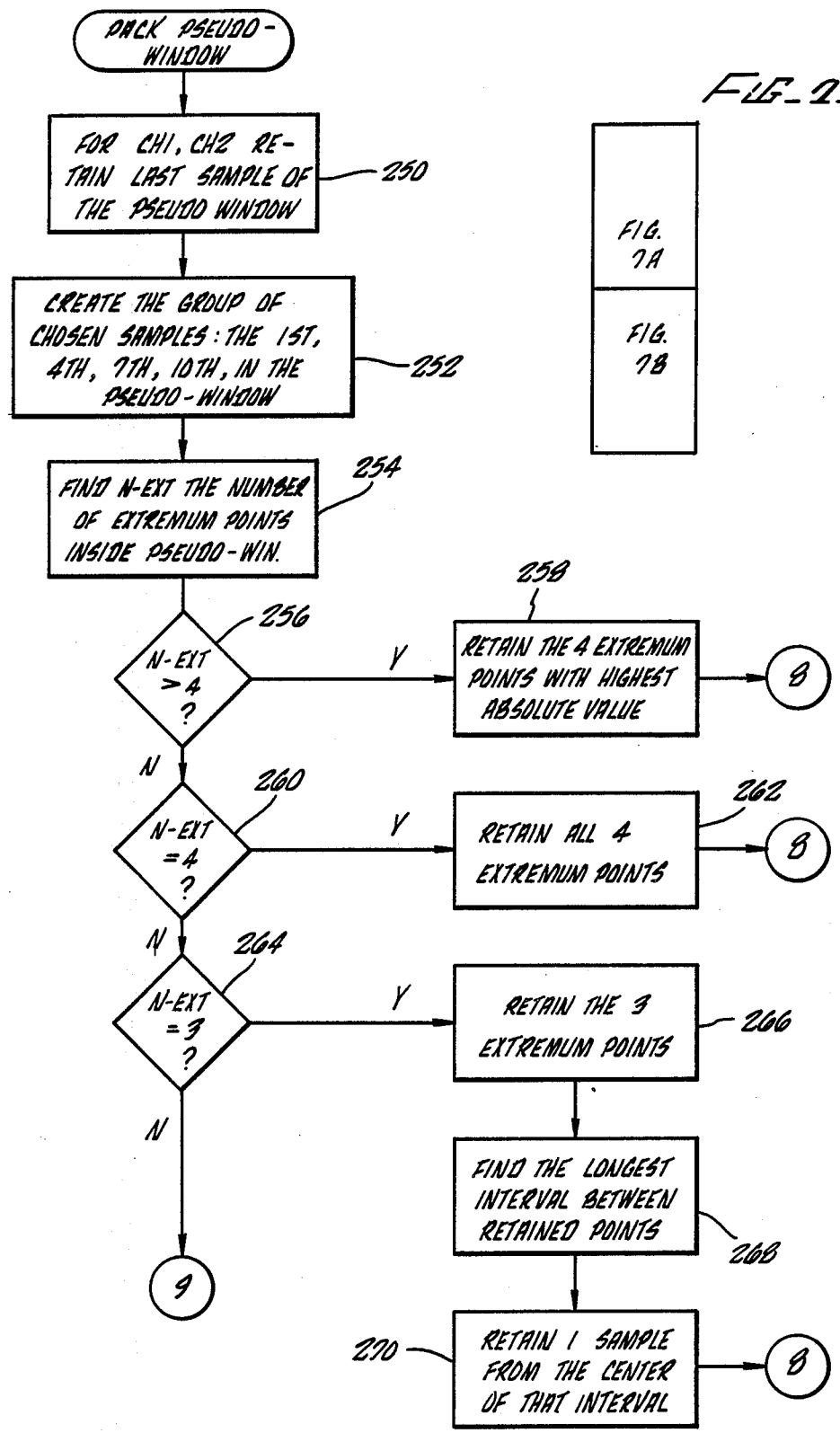
FIG. 2 is a flow diagram showing the sampling procedure used in a preferred embodiment of the present invention, using doublebuffering.
Figure 2A:
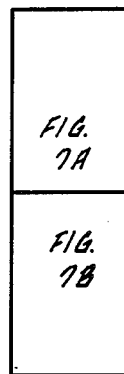

Referring now to FIG. 2, a flow diagram of a sampling routine according to a preferred embodiment of the present invention, an initialization routine 100 serves to reset flags and do other housekeeping tasks readily understood by those of ordinary skill in the art. Channel 1 is then sampled at 102 at the sampling rate S. The sampled value of the data in channel 1 is then stored in the current buffer portion of the input data input buffer 22 at 104. Next the signal on channel 2 is sampled at 106, and its sampled value is stored in the current buffer portion of data input buffer 24 at step 108. At 110, it is determined whether the current buffer is full. If not, steps 102, 104, 106, and 108 are repeated. If the current buffer is full the current-buffer-full flag is set at 112 and the other buffer portion of the dual buffer is activated at 114. The sampling procedure then starts again, this time using the other portions of dual data input buffers 22 and 24.

Referring now to FIG. 3, a main program loop executed by the microprocessor according to a preferred embodiment of the present invention repeatedly tests for the current-buffer-full flag 112 (of FIG. 2) at 120 until the flag indicates that the current buffer is full. When the current buffer is full, the main program switches to the pack buffer routine.

Referring now to FIG. 4, the packing of a buffer according to a preferred embodiment of the present invention is shown. At 150, the data input buffers 22 and 24 are examined, as previously disclosed, to designate windows and pseudo-windows for channel 1. At 152 the same procedure is performed for channel 2. At 154, a determination is made regarding which channel has the cleaner signal, according to the criteria previously described herein. If channel 1 has the cleaner signal, the windows and pseudo-windows are designated from channel 1 at 156. If, on the other hand, channel 2 has the cleaner signal, the windows and pseudo-windows are designated from channel 2 at 160.

Next, at 158, the index, a pointer to the locations in the input data buffers 22 and 24 is set to 0. At 162, a determination is made regarding whether the current index value denotes the location of the first byte of a window interval. If it does, the program switches to the routine for packing a window. If it does not, a decision is made at 164 as to whether the current index value denotes the start of a pseudo-window interval. If so, the program switches to the routine for packing a pseudo-window. If not, the program switches to the routine to pack the sample in S/R mode. At the end of each of the routines for packing, which will be discussed with respect to FIGS. 5 through 7, the index is incremented. A decision is made at 166 regarding whether the end of the input buffer being packed has been reached. If not, the routine returns to 162 to determine whether a window start is denoted by the current index value. If, on the other hand, the end of the data input buffers 22 and 24 have been reached, the program returns to the main program loop of FIG. 3.

The packing of a sample in S/R mode according to a preferred embodiment is shown with reference to FIG. 5. If an S/R mode sample is to be packed, the next sample is chosen to be the Rth sample away from sample indicated as the current sample, shown at 200. The value of the difference between the current sample and the last unpacked value is mapped into the range of −7:7 using the values of Table I. Those of ordinary skill in the art will readily recognize how the contents of Table I may be used in a computer program routine to map into the values shown in the Table. At 202, the two 4-bit nibbles, representing the mapped values for channels 1 and 2, are combined into a single 8-bit byte.

Next, at 204, this 8-bit byte is stored in an output buffer. Those of ordinary skill in the art will realize that, depending on the particular hardware configuration utilized, it may be more advantageous to store the entire group of these 8-bit bytes in such an output buffer and then write them into memory in one operation. On the other hand, in some cases it may be more advantageous to directly write the single 8-bit byte into memory at this point. It is simply a matter of design choice.

Next, at 206, the sample indicated as the current sample is updated so that the next time the operation at 200 is performed the program may select the Rth sample from the new current sample.

Next, at 208, the index value is updated and the routine returns to 166 of FIG. 4 to determine whether the end of the input buffer has been reached.

Referring now to FIG. 6, a preferred embodiment for packing a window is set forth. First, at 220, the reset counter is incremented. Next, at 222, a determination is made whether the current value of the reset counter equals a reset period. If so, at 224 a reset code is stored in the output buffer. If not, at 226 a window code is stored in the output buffer. Next, at 228, the difference between the next sample and the last value unpacked is calculated for both channels. That difference is then mapped into a range of −7:7 according to Table II and the last value unpacked is updated.

Next, the two 4-bit nibbles are combined into a single 8-bit byte at 230. At 232, the 8-bit byte is stored in the output buffer. Next, as previously mentioned, the index value is updated at 234. Finally, at 236, a determination is made as to whether the end of the window interval has been reached. If not, the routine loops back to step 228. If the window interval has ended, the program returns to step 166 of FIG. 4.

Finally, the packing of pseudo-window is shown in FIG. 7.

First, the data sample in the pseudo-window is retained at 250. Next, at 252 the group of the first, fourth, seventh, and tenth samples in the pseudo-window are chosen. At 254, the number N-Ext, the number of extremum points inside the pseudo-window is determined. At 256 it is determined whether N-Ext is greater than 4. If so, the 4 extrema points with the maximum absolute values are retained at 258. If not, at 260 it is determined whether N-Ext equals 4, if so, all extremum points are retained at 262. If N-Ext does not equal 4, whether N-Ext equals 3, is determined at 264. If yes, the three extremum points are retained at 266, the longest interval between retained points is determined at 268, and one sample from the center of that interval is retained at 270. If N-Ext does not equal 3 it is determined whether N-Ext equals 2 at 272. If so, two of the chosen samples are replaced by the extrema each extremum replacing the sample closest to it at 274. If not, it is determined whether N-Ext equals 1 at 276. If so, one of the chosen samples is replaced by the extremum such that the extremum replaces the sample closest to it at 278. If N-Ext does not equal 1 the retained samples are packed at 280 as if in S/R mode, using the Table III to map the pseudo-window into the range −7:7.

Upon the completion of the process loops shown in FIGS. 2 through 7, the full buffer portions of data input buffers 22 and 24 have been packed, either directly into memory, or into an output buffer which is then downloaded into memory. This process is then repeated until all of the memory locations have been filled. At this point, suitable means, apparent to anyone of ordinary skill in the art, may be employed to halt the data sampling and packing routines.

Attention is now drawn to FIG. 8, an illustrative ECG trace showing how a typical ECG signal is segmented into windows and pseudo-windows. FIG. 8 demonstrates how the windows and pseudo-windows are chosen such that they contain the area in the ECG where the signal changes are the greatest. As can be seen from FIG. 8, the ECG trace, denoted 300 is shown accompanied with designations of windows (W) at 302 and pseudo-windows (P) shown at 304. The trace 306 is merely illustrative of the number and width of the window and pseudo-window areas.

When the data has been gathered, and is stored in the memory, it is now ready to be unpacked and analyzed. The unpacking process is basically the reverse of the packing process. The contents of the memory are read back into the processor, one 8-bit byte at a time. The 8-bit byte is separated into the two original 4-bit nibbles. The nibbles are examined to detect the presence of any special codes. The data is then unpacked from the mapped value of −7:7 by substituting for that value by using the unpacked-to values in Table I as differences from the previous value as illustrated by Table I-a. In S/R mode, linear interpolation is used to reconstruct the intermediate samples.

When a special code is encountered, however, indicating the presence of a window or pseudo-window, the unpacking proceeds accordingly from either Table II or Table III until the correct number of bytes for either the window or the pseudo-window encountered have been unpacked. Linear interpolation is also used to fill in intermediate pseudo-window samples. The unpacking then proceeds according to Table I again, until another special code indicating window or pseudo-window interval is encountered. When the special code indicating the Reset Period is encountered, the next two 8-bit bytes are directly decoded as amplitude values which were encoded by the A/D converters.

As will be apparent to those of ordinary skill in the art, the present invention will function when data other than the 4-bit nibbles just described are stored. In fact, using the principles discussed herein, the data stored may be the 8-bit sample amplitude value itself. Similarly, the data stored may be another digital value related to either the amplitude of the sample or the differences between adjacent stored samples. Techniques, such as delta modulation, may be used to derive values related to the amplitude value of the sample for storage. Tables I, II, and III are examples of data stored related to the differences between samples, further providing a reconstructed amplitude value.

A preferred embodiment of the present invention has been disclosed. Those of ordinary skill in the art will readily perceive modifications and other embodiments which nevertheless are within the scope of the invention. It is intended that such other embodiments and modifications are covered herein and that the scope of the present invention is to be limited only by the appended claims.

What is claimed is:

1. A method of digitally storing electrocardiogram signals in solid state memory, including the steps of:
   (a) sampling analog electrocardiogram signals at a fixed sampling rate from at least one channel of an electrocardiogram apparatus,
   (b) converting each sampled signal to a multibit digital sample representing its amplitude,
   (c) calculating the differences in amplitude between each consecutive digital sample,
   (d) identifying a predetermined number of groups of a predetermined number of consecutive digital samples having the highest sums of the absolute values of said differences, (e) storing a number related to each digital sample from the ones of said predetermined number of groups, (f) storing a number related to every Rth digital sample from the digital samples outside of said predetermined number of groups, where R is an integer greater than one and is a function of the sampling rate.

2. The method of claim 1 wherein R is an integer between 2 and 6.

3. The method of claim 1 including the further step of storing a window-start code byte prior to storage of the first number related to each digital sample from each one of said predetermined number of groups.

4. The method of claim 1, including the further step of providing a reset byte every fixed number of seconds, immediately followed by a byte for each channel representing the present value of the amplitude of the sampled signal on that channel.

5. A method of digitally storing electrocardiogram signals in solid state memory, including the steps of:
(a) sampling analog electrocardiogram signals at a fixed sampling rate from at least one channel of an electrocardiogram apparatus,
(b) converting each sampled signal to a multibit digital sample representing its amplitude,
(c) calculating the differences in amplitude between each consecutive digital sample,
(d) identifying groups of a predetermined number of consecutive digital samples wherein the sums of the absolute values of said differences exceed a predetermined threshold,
(e) storing each digital sample from said groups,
(f) storing every Rth digital sample from the digital samples outside of said groups, where R is an integer greater than one and is a function of the sampling rate.

6. The method of claim 5 wherein R is an integer between 2 and 6.

7. The method of claim 5 including the further step of storing a window-start code byte immediately prior to storage of the first digital sample from each one of said groups, 8. The method of claim 5, including the further step of providing a reset byte every fixed number of seconds, immediately followed by a byte for each channel representing the present value of the amplitude of the sampled signal on that channel.

9. A method of digitally storing electrocardiogram signals in solid state memory, including the steps of:
(a) sampling analog electrocardiogram signals at a fixed sampling rate from at least one channel of an electrocardiogram apparatus,
(b) converting each sampled signal to a multibit digital sample representing its amplitude,
(c) calculating the differences in amplitude between each consecutive digital sample,
(d) identifying groups of a predetermined number of consecutive digital samples wherein the sums of the absolute values of said differences exceed a predetermined threshold,
(e) storing a number related to each digital sample from said groups,
(f) storing a number related to every Rth digital sample from the digital samples outside of said groups, where R is an integer greater than one and is a function of the sampling rate.

10. The method of claim 9 wherein R is an integer between 2 to 6.

11. The method of claim 9 including the further steps of: storing a window-start code byte immediately prior to storage of the first digital sample from each one of said groups.

12. The method of claim 9, including the further step of providing a reset byte every fixed number of seconds, immediately followed by a byte for each channel representing the present value of the amplitude of the sampled signal on that channel.

13. A method of digitally storing electrocardiogram signals in solid state memory, including the steps of:
(a) sampling analog electrocardiogram signals at a fixed sampling rate from at least one channel of an electrocardiogram apparatus,
(b) converting each sampled signal to a multibit digital sample representing its amplitude,
(c) calculating the differences in amplitude between each consecutive digital sample,
(d) identifying groups of a predetermined number of consecutive digital samples wherein the sums of the absolute values of said differences exceed a predetermined threshold,
(e) storing from said groups a digital value related to the difference in amplitude between each digital sample and the digital sample preceding it,
(f) storing a digital value related to the difference in amplitude between every Rth digital sample from the digital samples outside of said groups, where R is an integer greater than one and is a function of the sampling rate.

14. The method of claim 13 wherein R is an integer between 2 and 6.

15. The method of claim 13 including the further steps of: storing a window-start code byte immediately prior to storage of the first digital sample from each one of said groups.

16. The method of claim 13, including the further step of providing a reset byte every fixed number of seconds, immediately followed by a byte for each channel representing the present value of the amplitude of the sampled signal on that channel.

17. A method of digitally storing electrocardiogram signals in solid state memory, including the steps of:
(a) sampling analog electrocardiogram signals at a fixed sampling rate from at least one channel of an electrocardiogram apparatus,
(b) converting each sampled signal to a multibit digital sample representing its amplitude,
(c) calculating the differences in amplitude between each consecutive digital sample,
(d) identifying a predetermined number of groups of a predetermined number of consecutive digital samples having the highest sums of the absolute values of said differences,
(e) storing from said predetermined number of groups, a digital value related to the difference in amplitude between each digital sample and the digital sample preceding it,
(f) storing a digital value related to the difference in amplitude between every Rth digital sample from the digital samples outside of said predetermined number of groups, where R is an integer greater than one and is a function of the sampling rate.

18. The method of claim 17 wherein R is an integer between 2 and 6.

19. The method of claim 17 including the further step of storing a window-start code byte prior to storage of the first digital value related to each digital sample from each one of said predetermined number of groups.

20. The method of claim 17 including the further step of providing a reset byte every fixed number of seconds, immediately followed by a byte for each channel representing the present value of the amplitude of the sampled signal on that channel.

21. A method of digitally storing electrocardiogram signals in solid state memory, including the steps of:
   (a) sampling analog electrocardiogram signals at a fixed sampling rate from at least one channel of an electrocardiogram apparatus,
   (b) converting each sampled signal to a multibit digital sample representing its amplitude,
   (c) calculating the differences in amplitude between each consecutive digital sample,
   (d) identifying a first predetermined number of groups of a predetermined number of consecutive digital samples having the highest sums of the absolute values of said differences,
   (e) storing a number related to each digital sample from said predetermined number of groups,
   (f) identifying a second predetermined number of groups of a predetermined number of consecutive samples having sums of the absolute values of said differences which exceed a predetermined threshold,
   (g) storing a number related to selected digital samples from said second predetermined number of groups,
   (h) storing a number related to every Rth digital sample from the digital samples outside of said first predetermined number of groups and said second predetermined number of groups, where R is an integer greater than one and is a function of the sampling rate.

22. The method of claim 21 wherein R is an integer between 2 and 6.

23. The method of claim 21 including the further steps of:
   storing a window-start code byte immediately prior to storage of the first number related to each digital sample from each one of said first predetermined number of groups, and,
   storing a pseudo-window start code byte immediately prior to storage of the first number related to selected digital samples from said second predetermined number of groups.

24. The method of claim 21, including the further step of providing a reset byte every fixed number of seconds, immediately followed by a byte for each channel representing the present value of the amplitude of the sampled signal on that channel.

25. A method of digitally storing electrocardiogram signals in solid state memory, including the steps of:
   (a) sampling analog electrocardiogram signals at a fixed sampling rate from at least one channel of an electrocardiogram apparatus,
   (b) converting each sampled signal to a multibit digital sample representing its amplitude,
   (c) calculating the differences in amplitude between each consecutive digital sample,
   (d) identifying a first predetermined number of groups of a predetermined number of consecutive digital samples having the highest sums of the absolute values of said differences,
   (e) storing each digital sample from said first predetermined number of groups,
   (f) identifying a second predetermined number of groups of a predetermined number of consecutive samples having sums of the absolute values of said differences which exceed a predetermined threshold,
   (g) storing selected digital samples from said second predetermined number of groups,
   (h) storing every Rth digital sample from the digital samples outside of said first predetermined number of groups and said second predetermined number of groups, where R is an integer greater than one and is a function of the sampling rate.

26. The method of claim 25 wherein R is an integer between 2 and 6.

27. The method of claim 25 including the further steps of:
   storing a window-start code byte immediately prior to storage of the first digital sample from each one of said first predetermined number of groups, and,
   storing a pseudo-window start code byte immediately prior to storage of the first of the selected digital samples from said second predetermined number of groups.

28. The method of claim 27, including the further step of providing a reset byte every fixed number of seconds, immediately followed by a byte for each channel representing the present value of the amplitude of the sampled signal on that channel.

29. A method of digitally storing electrocardiogram signals in solid state memory, including the steps of:
   (a) sampling analog electrocardiogram signals at a fixed sampling rate from at least one channel of an electrocardiogram apparatus,
   (b) converting each sampled signal to a multibit digital sample representing its amplitude,
   (c) calculating the differences in amplitude between each consecutive digital sample,
   (d) identifying a first predetermined number of groups of a predetermined number of consecutive digital samples having the highest sums of the absolute values of said differences,
   (e) storing from said first predetermined number of groups, a digital value related to the difference in amplitude between each digital sample and the digital sample preceding it,
   (f) identifying a second predetermined number of groups of a predetermined number of consecutive samples having sums of the absolute values of said differences which exceed a predetermined threshold,
   (g) storing a digital value relates to the difference in amplitude between selected digital samples from the second predetermined number of groups,
   (h) storing a digital value related to the difference in amplitude between every Rth digital sample from the digital samples outside of said first predetermined number of groups and said second predetermined number of groups, where R is an integer greater than one and is a function of the sampling rate.

30. The method of claim 29 wherein R is an integer between 2 and 6.

31. The method of claim 29 including the further steps of:

storing a window-start code byte immediately prior to storage of the first digital sample from each one of said first predetermined number of groups, and, storing a pseudo-window start code byte immediately prior to storage of the first of the digital values related to the difference in amplitude between selected digital samples from said second predetermined number of groups.

32. The method of claim 29, including the further step of providing a reset byte every fixed number of seconds, immediately followed by a byte for each channel representing the present value of the amplitude of the sampled signal on that channel.

33. A method of digitally storing electrocardiogram signals in solid state memory, including the steps of:
  (a) sampling analog electrocardiogram signals at a fixed sampling rate from two channels of an electrocardiogram apparatus,
  (b) converting each sampled signal to a multibit digital sample representing its amplitude,
  (c) calculating the differences in amplitude between each consecutive digital sample,
  (d) identifying a selected channel having the fewest artifacts,
  (e) identifying from said selected channel a predetermined number of groups of a predetermined number of consecutive digital samples having the highest sums of the absolute values of said differences,
  (f) storing a number related to each digital sample from the ones of said predetermined number of groups,
  (g) storing a number related to every Rth digital sample from the digital samples outside of said predetermined number of groups, where R is an integer greater than one and is a function of the sampling rate.

34. The method of claim 33 wherein R is an integer between 2 and 6.

35. The method of claim 33 including the further step of storing a window-start code byte prior to storage of the first number related to each digital sample from each one of said first predetermined number of groups.

36. The method of claim 33, including the further step of providing a reset byte every fixed number of seconds, immediately followed by a byte for each channel representing the present value of the amplitude of the sampled signal on that channel.

37. A method of digitally storing electrocardiogram signals in solid state memory, including the steps of:
  (a) sampling analog electrocardiogram signals at a fixed sampling rate from two channels of an electrocardiogram apparatus,
  (b) converting each sampled signal to a multibit digital sample representing its amplitude,
  (c) calculating the differences in amplitude between each consecutive digital sample,
  (d) identifying a selected channel having the fewest artifacts,
  (e) identifying from said selected channel a predetermined number of groups of a predetermined number of consecutive digital samples having the highest sums of the absolute values of said differences,
  (f) storing each digital sample from the ones of said predetermined number of groups,
  (g) storing every Rth digital sample from the digital samples outside of said predetermined number of groups, where R is an integer greater than one and is a function of the sampling rate.

38. The method of claim 37 wherein R is an integer between 2 and 6.

39. The method of claim 37 including the further step of storing a window-start code byte prior to storage of the first digital sample from each one of said first predetermined number of groups.

40. The method of claim 37, including the further step of providing a reset byte every fixed number of seconds, immediately followed by a byte for each channel representing the present value of the amplitude of the sampled signal on that channel.

41. A method of digitally storing electrocardiogram signals in solid state memory, including the steps of:
  (a) sampling analog electrocardiogram signals at a fixed sampling rate from two channels of an electrocardiogram apparatus,
  (b) converting each sampled signal to a multibit digital sample representing its amplitude,
  (c) calculating the differences in amplitude between each consecutive digital sample,
  (d) identifying a selected channel having the fewest artifacts,
  (e) identifying from said selected channel a predetermined number of groups of a predetermined number of consecutive digital samples having the highest sums of the absolute values of said differences,
  (f) storing from said predetermined number of groups, a digital value related to the difference in amplitude between each digital sample and the digital sample preceding it,
  (g) storing a digital value related to the difference in amplitude between every Rth digital sample from the digital samples outside of said predetermined number of groups, where R is an integer greater than one and is a function of the sampling rate.

42. The method of claim 41 wherein R is an integer between 2 and 6.

43. The method of claim 42 including the further step of storing a window-start code byte prior to storage of the first digital value from each one of said first predetermined number of groups.

44. The method of claim 42, including the further step of providing a reset byte every fixed number of seconds, immediately followed by a byte for each channel representing the present value of the amplitude of the sampled signal on that channel.

45. A method of digitally storing electrocardiogram signals in solid state memory, including the steps of:
  (a) sampling analog electrocardiogram signals at a fixed sampling rate from two channels of an electrocardiogram apparatus,
  (b) converting each sampled signal to a multibit digital sample representing its amplitude,
  (c) calculating the differences in amplitude between each consecutive digital sample,
  (d) identifying a selected channel having the fewest artifacts,
  (e) identifying from said selected channel a first predetermined number of groups of a predetermined number of consecutive digital samples having the highest sums of the absolute values of said differences,
  (f) storing a number related to each digital sample from said first predetermined number of groups,
  (g) identifying a second predetermined number of groups of a predetermined number of consecutive samples having sums of the absolute values of said differences which exceed a predetermined threshold,
(h) storing a number related to selected digital samples from said second predetermined number of groups,
(i) storing a number related to every Rth digital sample from the digital samples outside of said first predetermined number of groups and said second predetermined number of groups, where R is an integer greater than one and is a function of the sampling rate.

46. The method of claim 45 wherein R is an integer between 2 and 6.

47. The method of claim 45 including the further steps of:
storing a window-start code byte immediately prior to storage of the first number related to each digital sample from each one of said first predetermined number of groups, and,
storing a pseudo-window start code byte immediately prior to storage of the first of the numbers related to said selected digital samples from said second predetermined number of groups.

48. The method of claim 45, including the further step of providing a reset byte every fixed number of seconds, immediately followed by a byte for each channel representing the present value of the amplitude of the sampled signal on that channel.

49. A method of digitally storing electrocardiogram signals in solid state memory, including the steps of:
(a) sampling analog electrocardiogram signals at a fixed sampling rate from two channels of an electrocardiogram apparatus,
(b) converting each sampled signal to a multibit digital sample representing its amplitude,
(c) calculating the differences in amplitude between each consecutive digital sample,
(d) identifying a selected channel having the fewest artifacts,
(e) identifying from said selected channel a first predetermined number of groups of a predetermined number of consecutive digital samples having the highest sums of the absolute values of said differences,
(f) storing each digital sample from said first predetermined number of groups,
(g) identifying a second predetermined number of groups of a predetermined number of consecutive samples having sums of the absolute values of said differences which exceed a predetermined threshold,
(h) storing selected digital samples from said second predetermined number of groups,
(i) storing every Rth digital sample from the digital samples outside of said first predetermined number of groups and said second predetermined number of groups, where R is an integer greater than one and is a function of the sampling rate.

50. The method of claim 49 wherein R is an integer between 2 and 6.

51. The method of claim 49 including the further steps of:
storing a window-start code byte immediately prior to storage of the first digital sample from each one of said first predetermined number of groups, and,
storing a pseudo-window start code byte immediately prior to storage of the first of the selected digital samples from said second predetermined number of groups.

52. The method of claim 49, including the further step of providing a reset byte every fixed number of seconds, immediately followed by a byte for each channel representing the present value of the amplitude of the sampled signal on that channel.

53. A method of digitally storing electrocardiogram signals in solid state memory, including the steps of:
(a) sampling analog electrocardiogram signals at a fixed sampling rate from at least one channel of an electrocardiogram apparatus,
(b) converting each sampled signal to a multibit digital sample representing its amplitude,
(c) calculating the differences in amplitude between each consecutive digital sample,
(d) identifying a selected channel having the fewest artifacts,
(e) identifying from said selected channel a first predetermined number of groups of a predetermined number of consecutive digital samples having the highest sums of the absolute values of said differences,
(f) storing from said first predetermined number of groups a digital value related to the difference in amplitude between each digital sample and the digital sample preceding it,
(g) identifying a second predetermined number of groups of a predetermined number of consecutive samples having sums of the absolute values of said differences which exceed a predetermined threshold,
(h) storing a digital value related to the difference in amplitude between selected digital samples from said second predetermined number of groups,
(i) storing a digital value related to the difference in amplitude between every Rth digital sample from the digital samples outside of said first predetermined number of groups and said second predetermined number of groups, where R is an integer greater than one and is a function of the sampling rate.

54. The method of claim 53 wherein R is an integer between 2 and 6.

55. The method of claim 53 including the further steps of:
storing a window-start code byte immediately prior to storage of the first digital value from each one of said first predetermined number of groups, and,
storing a pseudo-window start code byte immediately prior to storage of the first of the digital values related to the differences in amplitude between selected digital samples from said second predetermined number of groups.

56. The method of claim 53, including the further step of providing a reset byte every fixed number of seconds, immediately followed by a byte for each channel representing the present value of the amplitude of the sampled signal on that channel.

57. A method of digitally storing electrocardiogram signals in solid state memory, including the steps of:
(a) sampling analog electrocardiogram signals at a fixed sampling rate of at least 100 samples per second from at least one channel of an electrocardiogram apparatus,
(b) converting each sampled signal to a multibit digital sample representing its amplitude, (c) calculating the differences in amplitude between each consecutive digital sample, (d) identifying a predetermined number of groups of a predetermined number of consecutive digital samples having the highest sums of the absolute values of said differences, (e) referencing a first table for said predetermined number of groups, said table having a series of ranges of said differences in amplitude between consecutive digital samples, wherein each range corresponds to a mapped value and an unpacked-to value, (f) storing, for each sample from the ones of said predetermined number of groups, the mapped value from said first table corresponding to the one in said series of ranges within which the difference between said sample and the unpacked-to value for the immediately previously stored sample falls, (g) referencing a second table for said digital samples outside of said predetermined number of groups, said table having a series of ranges of said differences in amplitude between consecutive digital samples, wherein each range corresponds to a mapped value and an unpacked-to value, (h) storing, for each Rth sample from said samples outside of said predetermined number of groups, the mapped value from said second table corresponding to the one in said series of ranges within which the difference between said sample and the unpacked-to value for the immediately previously stored sample falls, wherein R is an integer greater than one and is a function of the sampling rate.

58. The method of claim 57 wherein R is an integer between 2 and 6.

59. The method of claim 57 including the further steps of:
storing a window-start code byte immediately prior to storage of the first mapped value from each one of said predetermined number of groups.

60. The method of claim 57, including the further step of providing a reset byte every fixed number of seconds, immediately followed by a byte for each channel representing the present value of the amplitude of the sampled signal on that channel.

61. A method of digitally storing electrocardiogram signals in solid state memory, including the steps of:

(a) sampling analog electrocardiogram signals at a fixed sampling rate of at least 100 samples per second from at least one channel of an electrocardiogram apparatus, (b) converting each sampled signal to a multibit digital sample representing its amplitude, (c) calculating the differences in amplitude between each consecutive digital sample, (d) identifying a predetermined number of groups of a predetermined number of consecutive digital samples having the highest sums of the absolute values of said differences, (e) referencing a first table for said first predetermined number of groups, said table having a series of ranges of said differences in amplitude between consecutive digital samples, wherein each range corresponds to a mapped value and an unpacked-to value, (f) storing, for each sample from the ones of said predetermined number of groups, the mapped value from said first table corresponding to the one in said series of ranges within which the difference between said sample and the unpacked-to value for the immediately previously stored sample falls, (g) identifying a second predetermined number of groups of a predetermined number of consecutive samples having sums of the absolute values of said differences which exceed a predetermined threshold, (h) referencing a second table for said second predetermined number of groups, said table having a series of ranges of said differences in amplitude between consecutive digital samples, wherein each range corresponds to a mapped value and an unpacked-to value, (i) storing, for selected samples from said second predetermined number of groups, the mapped value from said second table corresponding to the one in said series of ranges within which the difference between said sample and the unpacked-to value for the immediately previously stored sample falls, (j) referencing a third table for said digital samples outside of said first predetermined number of groups and said second predetermined number of groups, said table having a series of ranges of said differences in amplitude between consecutive digital samples, wherein each range corresponds to a mapped value and an unpacked-to value, (k) storing, for each Rth sample from said samples outside of said first predetermined number of groups and said second predetermined number of groups, the mapped value from said third table corresponding to the one in said series of ranges within which the difference between said sample and the unpacked-to value for the immediately previously stored sample falls, wherein R is an integer greater than one and is a function of the sampling rate.

62. The method of claim 61 wherein R is an integer between 2 and 6.

63. The method of claim 61 including the further steps of:
storing a window-start code byte immediately prior to storage of the first mapped value from each one of said first predetermined number of groups, and,
storing a pseudo-window start code byte immediately prior to storage of the first mapped value from said second predetermined number of groups.

64. The method of claim 61, including the further step of providing a reset byte every fixed number of seconds, immediately followed by a byte for each channel representing the present value of the amplitude of the sampled signal on that channel.

65. A method of digitally storing episodic signals in solid state memory, including the steps of:

(a) sampling analog episodic signals at a fixed sampling rate, (b) converting each sampled signal to a multibit digital sample representing its amplitude, (c) calculating the differences in amplitude between each consecutive digital sample, (d) identifying a predetermined number of groups of a predetermined number of consecutive digital samples having the highest sums of the absolute values of said differences, (e) storing a number related to each digital sample from the ones of said predetermined number of groups, (f) storing a number related to every Rth digital sample from the digital samples outside of said predetermined number of groups, where R is an integer greater than one and is a function of the sampling rate.

66. The method of claim 65 including the further step of storing a window-start code byte prior to storage of the first number related to each digital sample from each one of said first predetermined number of groups.

67. The method of claim 65, including the further step of providing a reset byte every fixed number of seconds, immediately followed by a byte representing the present value of the amplitude of the sampled signal.

68. A method of digitally storing episodic signals in solid state memory, including the steps of:
   (a) sampling analog episodic signals at a fixed sampling rate,
   (b) converting each sampled signal to a multibit digital sample representing its amplitude,
   (c) calculating the differences in amplitude between each consecutive digital sample,
   (d) identifying a first predetermined number of groups of a predetermined number of consecutive digital samples having the highest sums of the absolute values of said differences,
   (e) storing a number related to each digital sample from said first predetermined number of groups,
   (f) identifying a second predetermined number of groups of a predetermined number of consecutive samples having sums of the absolute values of said differences which exceed a predetermined threshold,
   (g) storing a number related to selected digital samples from said second predetermined number of groups,
   (h) storing a number related to every Rth digital sample from the digital samples outside of said first predetermined number of groups and said second predetermined number of groups, where R is an integer greater than one and is a function of the sampling rate.

69. The method of claim 68 including the further steps of:
   storing a window-start code byte immediately prior to storage of the first number related to each digital sample from each one of said first predetermined number of groups, and,
   storing a pseudo-window start code byte immediately prior to storage of the first number related to selected digital samples from said second predetermined number of groups.

70. The method of claim 68, including the further step of providing a reset byte every fixed number of seconds, immediately followed by a byte representing the present value of the amplitude of the sampled signal.

71. A method of digitally storing episodic signals in solid state memory, including the steps of:
   (a) sampling analog episodic signals at a fixed sampling rate,
   (b) converting each sampled signal to a multibit digital sample representing its amplitude,
   (c) calculating the differences in amplitude between each consecutive digital sample,
   (d) identifying a first predetermined number of groups of a predetermined number of consecutive digital samples having the highest sums of the absolute values of said differences,
   (e) storing each digital sample from said first predetermined number of groups,
   (f) identifying a second predetermined number of groups of a predetermined number of consecutive samples having sums of the absolute values of said differences which exceed a predetermined threshold,
   (g) storing selected digital samples from said second predetermined number of groups,
   (h) storing every Rth digital sample from the digital samples outside of said first predetermined number of groups and said second predetermined number of groups, where R is an integer greater than one and is a function of the sampling rate.

72. The method of claim 71 including the further steps of:
   storing a window-start code byte immediately prior to storage of the first digital sample from each one of said first predetermined number of groups, and,
   storing a pseudo-window code start byte immediately prior to storage of the first of the selected digital samples from each of said second predetermined number of groups.

73. The method of claim 71, including the further step of providing a reset byte every fixed number of seconds, immediately followed by a byte representing the present value of the amplitude of the sampled signal.

74. A method of digitally storing episodic signals in solid state memory, including the steps of:
   (a) sampling analog episodic signals at a fixed sampling rate,
   (b) converting each sampled signal to a multibit digital sample representing its amplitude,
   (c) calculating the differences in amplitude between each consecutive digital sample,
   (d) identifying a predetermined number of groups of a predetermined number of consecutive digital samples having the highest sums of the absolute values of said differences,
   (e) storing from said predetermined number of groups, a digital value related to the difference in amplitude between each digital sample and the digital sample preceding it,
   (f) storing a digital value related to the difference in amplitude between every Rth digital sample from the digital samples outside of said predetermined number of groups, where R is an integer greater than one and is a function of the sampling rate.

75. The method of claim 74 including the further step of storing a window-start code byte prior to storage of the first digital value from each one of said first predetermined number of groups.

76. The method of claim 74, including the further step of providing a reset byte every fixed number of seconds, immediately followed by a byte representing the present value of the amplitude of the sampled signal.

77. A method of digitally storing episodic signals in solid state memory, including the steps of:
   (a) sampling analog episodic signals at a fixed sampling rate,
   (b) converting each sampled signal to a multibit digital sample representing its amplitude,
   (c) calculating the differences in amplitude between each consecutive digital sample,
   (d) identifying from said selected channel a first predetermined number of groups of a predetermined number of consecutive digital samples having the highest sums of the absolute values of said differences,
(e) storing from said first predetermined number of groups a digital value related to the difference in amplitude between each digital sample and the digital sample preceding it.
(f) identifying a second predetermined number of groups of a predetermined number of consecutive samples having sums of the absolute values of said differences which exceed a predetermined threshold,
(g) storing a digital value related to the difference in amplitude between selected digital samples from said second predetermined number of groups,
(h) storing a digital value related to the difference in amplitude between every Rth digital sample from the digital samples outside of said first predetermined number of groups and said second predetermined number of groups, where R is an integer between 2 and 6.

78. The method of claim 77 including the further steps of:
storing a window-start code byte immediately prior to storage of the first digital value from each one of said first predetermined number of groups, and,
storing a pseudo-window start code byte immediately prior to storage of the first of the digital values related to the differences in amplitude between selected digital samples from each of said second predetermined number of groups.

79. The method of claim 77, including the further step of providing a reset byte every fixed number of seconds, immediately followed by a byte representing the present value of the amplitude of the sampled signal.

80. A method of digitally storing episodic signals in solid state memory, including the steps of:
(a) sampling analog episodic signals at a fixed sampling rate,
(b) converting each sampled signal to a multibit digital sample representing its amplitude,
(c) calculating the differences in amplitude between each consecutive digital sample,
(d) identifying a predetermined number of groups of a predetermined number of consecutive digital samples having the highest sums of the absolute values of said differences,
(e) referencing a first table for said predetermined number of groups, said table having a series of ranges of said differences in amplitude between consecutive digital samples, wherein each range corresponds to a mapped value and an unpacked-to value,
(f) storing, for each sample from the ones of said predetermined number of groups, the mapped value from said first table corresponding to the one in said series of ranges within which the difference between said sample and the unpacked-to value for the immediately previously stored sample falls,
(g) referencing a second table for said digital samples outside of said predetermined number of groups, said table having a series of ranges of said differences in amplitude between consecutive digital samples, wherein each range corresponds to a mapped value and an unpacked-to value,
(h) storing, for each Rth sample from said samples outside of said predetermined number of groups, the mapped value from said second table corresponding to the one in said series of ranges within which the difference between said sample and the unpacked-to value for the immediately previously stored sample falls, wherein R is an integer greater than one and is a function of the sampling rate.

81. The method of claim 80 including the further steps of:
storing a window-start code byte immediately prior to storage of the first mapped value from each one of said predetermined number of groups.

82. The method of claim 80, including the further step of providing a reset byte every fixed number of seconds, immediately followed by a byte representing the present value of the amplitude of the sampled signal.

83. A method of digitally storing electrocardiogram signals in solid state memory, including the steps of:
(a) sampling analog electrocardiogram signals at a fixed sampling rate,
(b) converting each sampled signal to a multibit digital sample representing its amplitude,
(c) calculating the differences in amplitude between each consecutive digital sample,
(d) identifying a first predetermined number of groups of a predetermined number of consecutive digital samples having the highest sums of the absolute values of said differences,
(e) referencing a first table for said first predetermined number of groups, said table having a series of ranges of said differences in amplitude between consecutive digital samples, wherein each range corresponds to a mapped value and an unpacked-to value,
(f) storing, for each sample from the ones of said predetermined number of groups, the mapped value from said first table corresponding to the one in said series of ranges within which the difference between said sample and the unpacked-to value for the immediately previously stored sample falls,
(g) identifying a second predetermined number of groups of consecutive samples having sums of the absolute values of said differences which exceed a predetermined threshold,
(h) referencing a second table for said second predetermined number of groups, said table having a series of ranges of said differences in amplitude between consecutive digital samples, wherein each range corresponds to a mapped value and an unpacked-to value,
(i) storing, for selected samples from said second predetermined number of groups, the mapped value from said second table corresponding to the one in said series of ranges within which the difference between said sample and the unpacked-to value for the immediately previously stored sample falls,
(j) referencing a third table for said digital samples outside of said first predetermined number of groups and said second predetermined number of groups, said table having a series of ranges of said differences in amplitude between consecutive digital samples, wherein each range corresponds to a mapped value and an unpacked-to value,
(k) storing, for each Rth sample from said samples outside of said predetermined number of groups and said second predetermined number of groups, the mapped value from said third table corresponding to the one in said series of ranges within which the difference between said sample and the unpacked-to value for the immediately previously stored sample falls, wherein R is an integer greater than one and is a function of the sampling rate.

84. The method of claim 83 including the further steps of:
storing a window-start code byte immediately prior to storage of the first mapped value from each one of said first predetermined number of groups, and,
storing a pseudo-window start code byte immediately prior to storage of the first mapped value from each of said second predetermined number of groups.

85. The method of claim 83, including the further step of providing a reset byte every fixed number of seconds, immediately followed by a byte representing the present value of the amplitude of the sampled signal.

86. Portable apparatus for digitally storing electrocardiogram signals in solid state memory, including:
input amplifier means for conditioning and amplifying analog electrocardiogram signals,
digitizing means, connecting to said input amplifier means, for converting said analog electrocardiogram signals to digital representations thereof,
buffer means, connected to said digitizing means, for temporarily storing a plurality of said digital representations,
processor means, communicating with said buffer means, for determining, from said plurality of digital representations, the existence of window and pseudo-window intervals therein and the data to be stored in accordance therewith, and for directing the storage of said date,
a dynamic random access memory, communicating with said buffer means and said processor means, having a plurality of storage locations, for storing said data,
circuit means for determining the temperature of said apparatus,
refresh control means, responsive to said circuit means, for controlling the refresh rate of DRAMs of said dynamic random access memory in response to the temperature of said apparatus.

87. The portable apparatus of claim 86 wherein said refresh control means controls the refresh rate of dynamic random access memory to be 150 mSec at 25° C. and 80 mSec at 45° C.

88. The portable apparatus of claim 87 wherein said refresh control means causes said refresh rate to vary approximately exponentially with temperature.

89. Portable apparatus for digitally storing electrocardiogram signals in solid state memory, including:
first and second input amplifier means for conditioning an amplifying analog electrocardiogram signals on a first and a second channel, respectively,
first and second digitizing means, connected to said first and second input amplifier means respectively, for converting said analog electrocardiogram signals to digital representations thereof,
first and second buffer means, connected to said first and second digitizing means respectively, for temporarily storing a plurality of said digital representations,
processor means, communicating with said first and second buffer means for determining which of the signals on said first and second channels has the fewest artifacts, for determining, from said plurality of digital representations, data to be stored, and for directing the storage of said data,
a dynamic random access memory, communicating with said buffer means and said processor means, having a plurality of storage locations, for storing said data,
circuit means for determining the temperature of said apparatus,
refresh control means, responsive to said circuit means, for controlling the refresh rate of DRAMs of said dynamic random access memory in response to the temperature of said apparatus.

90. The portable apparatus of claim 89 wherein said refresh control means controls the refresh rate of dynamic random access memory to be 150 mSec at 25° C. and 80 mSec at 45° C.

91. The portable apparatus of claim 89 wherein said refresh control means causes said refresh rate to vary approximately exponentially with temperature.

* * * * *